US00PP13634P29

(12) United States Plant Patent
Vardi et al.

(10) Patent No.: US PP13,634 P2
(45) Date of Patent: Mar. 11, 2003

(54) CITRUS TREE NAMED 'SHANI'

(75) Inventors: Aliza Vardi, Ramat Gan (IL); Pinchas Spiegel-Roy, Ramat-Gan (IL); Ahuva Frydman-Shani, Ramat-Gan (IL); Avraham Elchanati, Holon (IL)

(73) Assignee: State of Israel-Ministry of Agriculture and Rural Development, Tel Aviv (IL)

( * ) Notice: Subject to any disclaimer, the term of this patent is extended or adjusted under 35 U.S.C. 154(b) by 14 days.

(21) Appl. No.: 09/716,483

(22) Filed: Nov. 20, 2000

(51) Int. Cl.[7] ..... A01H 5/00

(52) U.S. Cl. ..... Plt./202

(58) Field of Search ..... Plt./202

(56) References Cited

PUBLICATIONS

GTITM UPOVROM Citation for 'Shani' as per IL PRB 01464; Feb. 26, 1999.*

GTITM UPOVROM Citation for 'Shani' as per ZA PBR 01376; Apr. 13, 1993.*

Spiegel–Roy, P.; Vardi, A.; 'Shani', 'Orah' and 'Winola'—Three New Selections from our Breeding Program; 7th International Citrus Congress Proceedings—International Society of Citriculture; The Society, vol. 1, 72–83; 1992 (notice only).*

* cited by examiner

*Primary Examiner*—Kent L. Bell
(74) *Attorney, Agent, or Firm*—Akerman Senterfitt

(57) ABSTRACT

A new variety of mandarin citrus is described that is distinguished by fruit having few seeds, a late fruit ripening period, red-orange fruit and an oblate shape.

2 Drawing Sheets

FIELD OF THE INVENTION

A new mandarin citrus tree *Citrus reticulata* hybrid is described. The new variety named 'Shani' is desirable to the consumer because of the red-orange color and excellent flavor of its fruit and to the commercial grower because of its late-season fruit ripening.

BACKGROUND OF THE NEW PLANT

The present invention relates to a new and distinct variety of mandarin citrus tree *Citrus reticulata* hybrid developed by inventors Pinchas Spiegel-Roy, Aliza Vardi, Avraham Elchanati and Ahuva Frydman-Shani in Bet Dagan, Israel from a controlled pollination cross between seed parent 'Wilking' (unpatented) mandarin and pollen parent 'Michal' (unpatented).

Asexual reproduction by conventional bud grafting of the new variety at the Agriculture Research Organization Volcani Center in Bet Dagan, Israel, has shown that the new characteristics are stabilized and permanently fixed through successive propagation.

The objective in breeding the present new tree variety, assigned the denomination 'Shani', was to obtain a late ripening citrus mandarin with few or no seeds. In the spring of 1976, the seed parent 'Wilking' (unpatented) mandarin (resulting from a cross of 'King'×'Willowleaf' (Mediterranean) reported by Frost in *Calif. Agr. Exp. Sta. Bull.* 1935, pp.597–601), was crossed with pollen parent 'Michal', a cultivar of Israeli origin believed to be a natural hybrid between two *Citrus reticulata* 'Blanco' cultivars. The fruit was collected in November 1977. Seeds were extracted and germinated in January 1978. About 400 seedlings were grown from the germinated seeds. Each seedling was grafted onto Sour orange nucellar rootstock.

Field planting was established from container grown plants in the spring of 1979. The first fruits were observed in February, 1983 and again in 1984.

One of the 400 plants was designated 46/2. The fruits of this scion were observed to be fully ripe during February to mid March. The fruit was red-orange in color with few seeds and excellent flavor.

Bud wood was taken from 46/2 and top grafted in the spring of 1984 on 8 Troyer nucellar rootstock The grafted plants were planted a year later in the experimental grove of the Agricultural Research Organization, Bet Dagan, Israel. The first crop of these trees was obtained in 1987. The yield of the scion grafted onto Troyer rootstock was good. The fruit was fully ripe the last week in February. The color of the fruit when fully ripe was orange-red, and the fruit was quite easy to peel. The fruit had a pleasant flavor and excellent aroma. The juice had a sugar concentration of about 12.8% and an acid concentration of about 1.09%.

SUMMARY OF THE INVENTION

46/2, designated 'Shani', is characterized by reddish-orange fruit having few seeds and flowers with anthers bearing viable pollen. Table 1 shows some of the characteristics of the new tree compared to the seed parent 'Wilking' and pollen parent 'Michal'. All observations were made in Israel on citrus 5–6 years old. Color designations have been determined from The RHS Colour Chart published by the Royal Horticultural Society, London.

TABLE 1

| Tree | Fruit skin color | Chromosome number | Seeds/fruit | Pollen fertility[1] |
|---|---|---|---|---|
| 46/2 'Shani' | Orange-red RHS 34A | 2n = 18 | 0–9 | 88% |
| 'Wilking' | Orange RHS 25A | 2n = 18 | 6–15 | 94% |
| 'Michal' | Orange-red RHS 33A | 2n = 18 | 2–9 | 86% |

[1]Estimated by Acetocarmine staining

Although 'Merav' (U.S. Plant patent application Ser. No. 09/716,984) and 'Shani' are sibling cultivars, they can be easily distinguished from each other as shown in Table 2.

TABLE 2

| | Time of fruit ripening | Fruit skin color | Fruit Flavor |
|---|---|---|---|
| 'Merav' | December–January | Orange RHS 30B | excellent |
| 'Shani' | Feb.–mid March | Orange-red RHS 34A | excellent aroma excellent |

The following is a detailed description of the new mandarin citrus variety based on observations made under typical Israeli grove conditions.

The leaf shape, tree size and shape of 'Shani' are intermediate between the seed parent 'Wilking' and the pollen parent 'Michal'. Young shoots have no anthocyanin coloration at the tip. The tree is quite productive with a slight tendency to alternate bearing (lower yield of fruit after a year of heavy bearing if fruit is not harvested). The canopy is moderately dense. The bark of the young shoots is initially smooth and green, gradually turning into a smooth brown-gray.

The chromosome number of the tree is diploid (2n=18) as is the chromosome number of the two parents.

The leaves somewhat resemble 'Michal' in size and shape. The leaf shape in cross section is slightly concave. Foliar flushes, as measured in Bet Dagan, Israel, occur between April and September. The firmness of the leave blade is relatively weak, without undulation. Petioles are without wings or have very narrow wings.

The characteristics of the flowering and the flower parts are similar to 'Michal'. The flower has almost the same size as the flower of 'Michal'. All flowers of mandarin cultivars are very much alike in color of petal (both sides are white), anthers, pistils, etc. Flowering as measured in Bet Dagan, Israel, occurs between mid March and the beginning of April. Terminal flower buds have no anthocyanin coloration. Anther color is yellow with 88% stainable pollen grain as obtained by staining with acetocarmine..

The fruit has few seeds, about 0 to 9 seeds per fruit. The fruit shape is oblate and medium in size. When 50 fruits were measured, the fruit had an average weight of 112 grams, an average height of 49 mm, and an average diameter of 65 mm. The fruit surface is usually smooth with a reddish-orange color, 34A, on The Royal Horticultural Society of London Colour Chart. Fruit ripening does not differ from outside of the canopy to the inside, but the fruit color of the outside canopy is a little brighter compared to the fruit color of the inside canopy. There is no persistence of the style and the areola is not completely developed. A small navel is usually present, similar to pollen parent 'Michal'. The rind is thin and relatively easy to peel.

The color of the albedo is reddish and the flesh is dark orange in color. The fruit contains 10–12 segments and is very juicy. The external color of the seed is white and the internal color is greyed-orange. The color of the cotyledons is greyed-green. The seed size, shape and texture are quite similar to that of 'Michal'. The seed size is medium. The fruit reaches maturity in February in Israel. The ripening of the fruit on the tree and within the fruit is uniform. Fruit remaining on the tree does not re-green and does begin to lose quality until March. The fruit has an attractive appearance and an excellent flavor and aroma.

DESCRIPTION OF THE PHOTOGRAPHS

The new citrus tree is illustrated in the accompanying color photographs.

Sheet one depicts the whole tree and canopy shape of the new variety.

Sheet two shows the exterior of the fruit as well as transverse midsections in a plane substqantially perpendicular to the axis, illustrating no seeds in the interior of the fruit.

DESCRIPTION OF THE NEW TREE

The following is a detailed description of the new mandarin citrus variety 'Shani' based on observations made under typical Israeli grove conditions.

Tree:

*Origin.*—Cross between seed parent 'Wilking' and pollen parent 'Michal'.

*Classification.*—Botanical: *Citrus reticulata* hybrid. Common: Mandarin citrus. Cultivar: 'Shani'.

*Shape.*—Upright, spreading.

*Thorns.*—Very small to medium (1–5 mm length).

*Branching.*—Upright.

*Canopy.*—Moderately dense.

*Bark.*—Immature: Smooth, green RHS 146A. Mature: Smooth, greyed-green, RHS 189A.

*Leaf.*—Shape: Long, lanceolate and taper pointer (77 mm length, 38 mm width. Leaf blade: Weak, without undulation ,section slightly concave. Petioles: Wingless or very narrow wings 9 mm length, 1.7 mm in diameter, Green RHS 146B. Color: Upper: Green RHS 146A; lower: Green RHS 146B. Foliar flushes: April–September.

*Habit.*—Moderately vigorous, round-topped.

*Height.*—2.5–3 m.

*Disease resistance.*—No particular susceptibility or resistance observed.

*Trunk diameter.*—38 cm at 20 cm above the ground.

*Winter hardiness.*—Winter temperature in Bet Dagan, Israel averages 4–7 degrees Centigrade.

Flower:

*Petals.*—5.

*Petal color.*—White RHS 155C.

*Flowering period.*—Mid March to early April (Israel).

*Flower drop.*—April.

*Stamens.*—Approximately 20.

*Anther color.*—Yellow RHS 8B.

*Pollen fertility.*—88% by acetocarmine staining.

*Anthocyanin coloration.*—No coloration.

Fruit:

*Shape.*—Oblate.
*Size.*—Medium.
*Weight.*—112 g (average of 50 fruits).
*Height.*—49 mm.
*Diameter.*—65 mm.
*Surface color.*—Red-orange RHS 34A.
*Rind oil gland.*—Conspicuous, average number (35 $cm^2$).
*Style.*—No persistence.
*Navel.*—Small navel similar to 'Michal' attached to the inner part of the peel (diameter: 6 mm, height 2–3 mm).
*Rind.*—Smooth, thin (2 mm) and easy to peel.
*Albedo.*—Orange RHS 24D.
*Areola.*—Incompletely developed.
*Fruit segments.*—10–12.
*Color of flesh.*—Orange RHS 25A.
*Time to maturity.*—February to mid-March (Israel).
*Productivity.*—35–40 kg per tree each season.
*Fruit extract.*—(Quality tested Feb. 21, 1994). Total soluble solids (TSS): 12.8%. Acid content: 1.09%. TSS/acid ratio: 11.8. Flavor and aroma: Excellent.

Seeds:

*Size.*—Medium (about 10 mm length, 6 mm wide).
*Color.*—External: White RHS 158D. Internal: Greyed-orange RHS 165B.
*Cotyledons.*—Greyed-green RHS 193C.
*Embryony.*—Polyembryony.

The tree and its fruit as described herein may vary somewhat in certain characteristics due to climatic and/or soil conditions under which the variety is grown.

What is claimed is:

1. A new and distinct variety of *Citrus reticulata* hybrid tree substantially as herein described and shown.

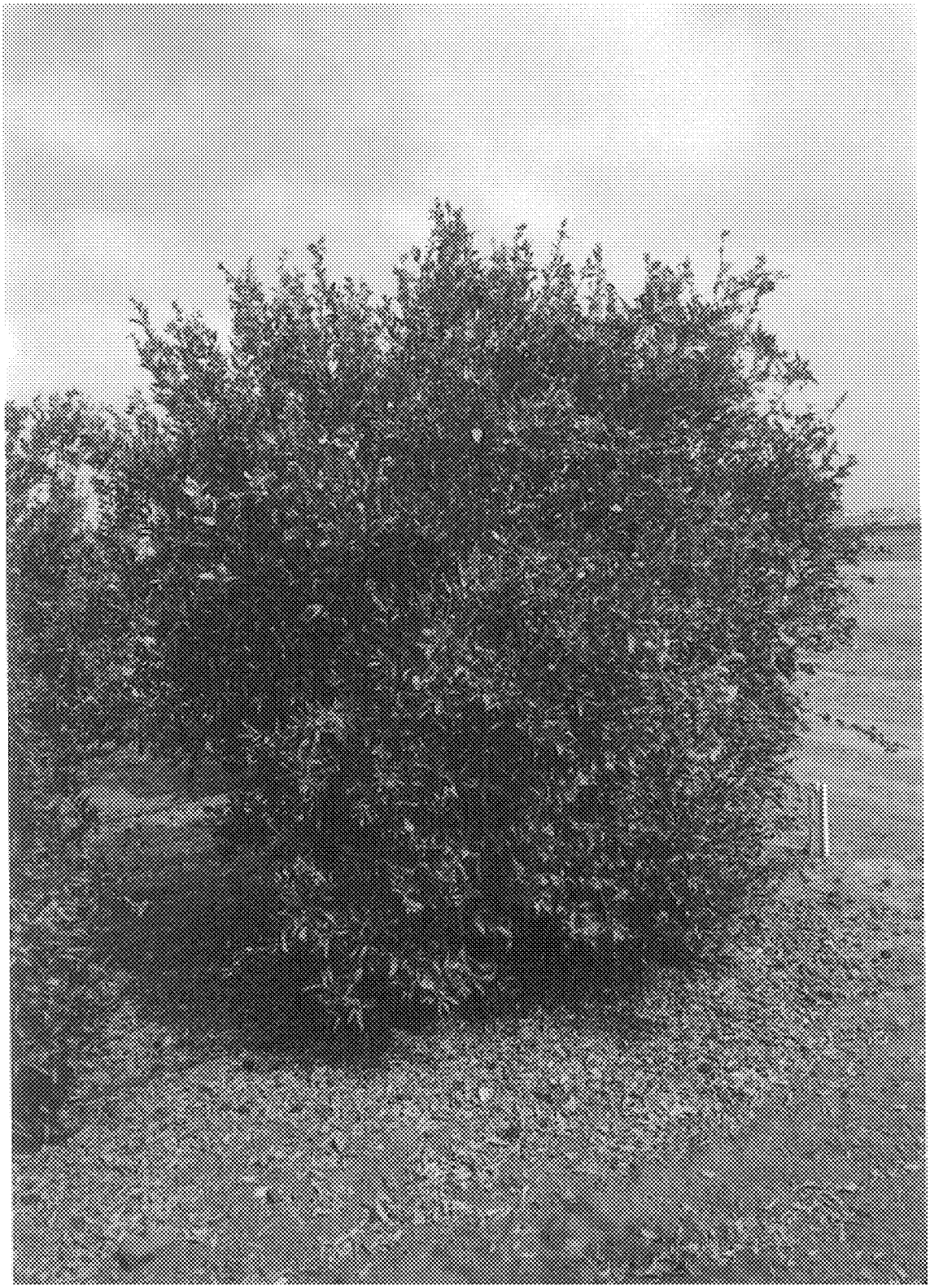

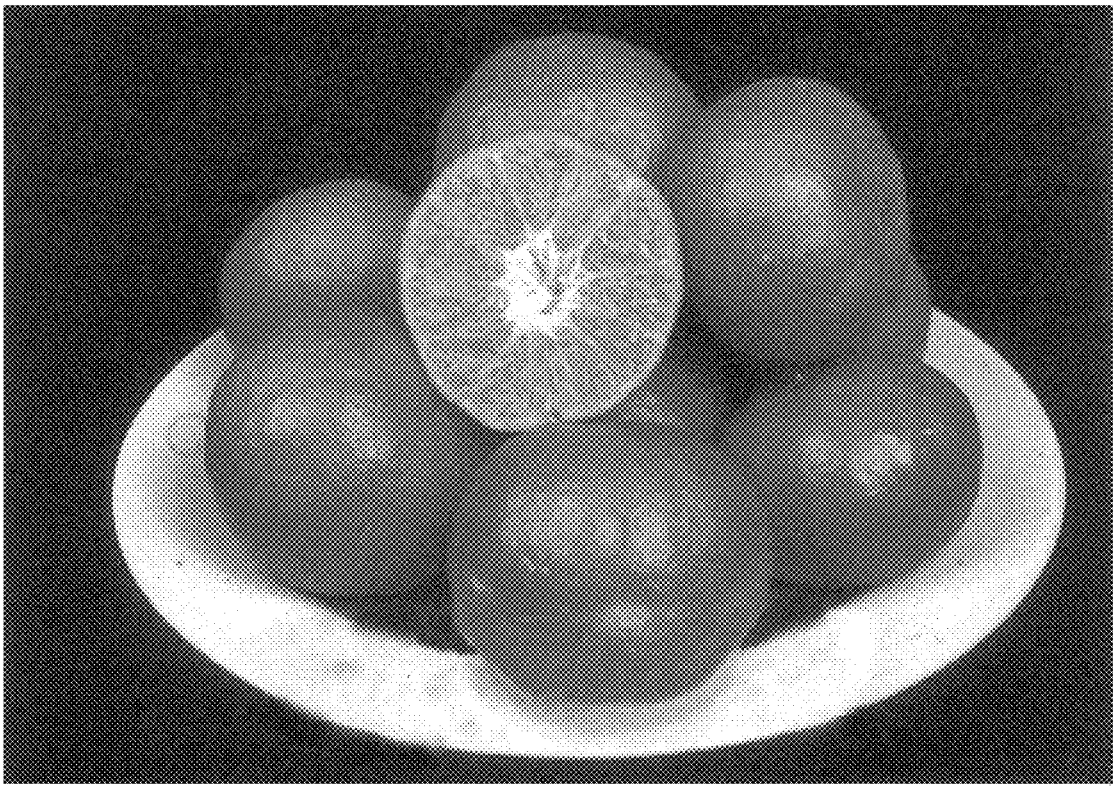

* * * * *